(12) United States Patent (10) Patent No.: US 8,453,977 B2
Zoland et al. (45) Date of Patent: *Jun. 4, 2013

(54) NEUTRAL FIELD TRAY SYSTEM

(75) Inventors: Mark P. Zoland, Scarsdale, NY (US);
Joseph Iraci, New Rochelle, NY (US)

(73) Assignee: Surgisure, LLC, New York, NY (US)

(*) Notice: Subject to any disclaimer, the term of this patent is extended or adjusted under 35 U.S.C. 154(b) by 129 days.

This patent is subject to a terminal disclaimer.

(21) Appl. No.: 13/098,745

(22) Filed: May 2, 2011

(65) Prior Publication Data

US 2011/0203957 A1 Aug. 25, 2011

Related U.S. Application Data

(63) Continuation-in-part of application No. 12/843,393, filed on Jul. 26, 2010, now Pat. No. 7,980,517, which is a continuation-in-part of application No. 12/430,396, filed on Apr. 27, 2009, now abandoned.

(51) Int. Cl.
*A47G 21/14* (2006.01)

(52) U.S. Cl.
USPC .... 248/37.6; 248/227.2; 248/318; 248/311.2; 206/571; 206/363; 206/352; 211/85.13

(58) Field of Classification Search
USPC ............ 248/121, 37.3, 37.6, 110, 207, 227.1, 248/227.2, 309.1, 318, 311.2; 206/210, 214, 206/571, 363, 438, 564, 352, 364, 365; 211/85.13
See application file for complete search history.

(56) References Cited

U.S. PATENT DOCUMENTS

| | | |
|---|---|---|
| D139,569 S | 11/1944 | O'Brien |
| 2,702,649 A | 2/1955 | Neilson |
| 2,717,505 A | 9/1955 | Andersson |
| 3,095,057 A | 6/1963 | Kraeling |
| 3,301,406 A | 1/1967 | Scott |
| 4,024,590 A | 5/1977 | Wendt |
| 4,730,725 A | 3/1988 | Marshall et al. |
| 5,170,804 A | 12/1992 | Glassman |
| D337,830 S | 7/1993 | Coyne et al. |
| 5,301,807 A | 4/1994 | Donahue |
| 5,339,955 A | 8/1994 | Horan et al. |
| 5,381,896 A | 1/1995 | Simons |
| 5,511,674 A | 4/1996 | Boyd et al. |
| 5,533,618 A | 7/1996 | Pickels, Jr. |
| 5,542,533 A | 8/1996 | Vargas |
| D376,943 S | 12/1996 | Czyszon |
| 5,779,053 A | 7/1998 | Partika et al. |
| 6,065,596 A | 5/2000 | Cavanagh |
| 6,095,057 A | 8/2000 | Corban |

(Continued)

OTHER PUBLICATIONS

Advanced Precautions for Today's O.R., Mark Davis, Handbook, 2001.

(Continued)

*Primary Examiner* — Bradley Duckworth
(74) *Attorney, Agent, or Firm* — Gordon & Jacobson, PC

(57) ABSTRACT

A neutral field tray includes a base with a width that tapers from a proximal end to a distal end, and an instrument trough at least partially recessed relative to the base and sized and configured to support at most a single surgical instrument. The trough is obliquely oriented relative to the base so as to present the proximal end of the instrument substantially above the base and to shield a sharp of the instrument within the trough. The tray also includes supporting structure for supporting the tray relative to a supporting surface.

20 Claims, 14 Drawing Sheets

U.S. PATENT DOCUMENTS

| | | |
|---|---|---|
| 6,193,932 B1 | 2/2001 | Wu et al. |
| 6,345,873 B1 | 2/2002 | Kim |
| 6,802,431 B2 | 10/2004 | Schinkel |
| 7,066,328 B2 | 6/2006 | Pulsifer |
| RE40,432 E | 7/2008 | Cavanagh |
| 7,441,655 B1 | 10/2008 | Hoftman |
| D608,015 S | 1/2010 | Sandel |
| D608,456 S | 1/2010 | Sandel |
| 7,665,606 B2 | 2/2010 | Gailard |
| 7,798,331 B2 | 9/2010 | Hardin et al. |
| 2005/0040066 A1 | 2/2005 | Pulsifer |
| 2005/0098460 A1 | 5/2005 | Smith et al. |
| 2009/0050516 A1 | 2/2009 | Hardin et al. |
| 2010/0270442 A1 | 10/2010 | Zoland |

OTHER PUBLICATIONS

Mayo Instrument Stands, Paragon Medical, catalog product descriptions, available at http://www.paragonmed.com/instrtables.shtml, downloaded Feb. 13, 2009.

Accessory Mayo Stand, catalog product description, DRE, available at http://www.dremed.com/catalog/product_info.php/products_id/325, downloaded Feb. 13, 2009.

Hands Free and Neutral Zone Solutions to Protect Against Sharps Injury and Potential Contamination, Sharps Safety Products, Sandel Medical Indistries, Lit #130227 Rev A011609.

Safe Handling of Sharps, Bulletin No. 1, Sandel Medical Insustries, #120226.05 (Sep. 2004).

NEUTRAL FIELD TRAY SYSTEM

CROSS-REFERENCE TO RELATED APPLICATIONS

This application is a continuation-in-part of U.S. Ser. No. 12/843,393, filed Jul. 26, 2010, now U.S. Pat. No. 7,980,517 which is a continuation-in-part of U.S. Ser. No. 12/430,396, filed Apr. 27, 2009, now abandoned both of which are hereby incorporated herein in their entireties by reference.

BACKGROUND OF THE INVENTION

1. Field of the Invention

This invention relates broadly to receptacles used in operating rooms for holding or temporarily storing surgical instruments. More particularly, this invention relates to surgical instrument receptacles used in conjunction with a mayo stand.

2. State of the Art

Instruments used by surgeons during surgical procedures are commonly laid out on a moveable table called a "mayo stand". A mayo stand includes a vertical leg, a rectangular frame horizontally cantilevered at the upper end of the leg, and a wheeled base at the lower end of the leg to provide mobility to the stand. A removable tray is seated on the frame. A typical mayo stand tray may be 13 inches wide by 19 inches long and is generally supported at its longitudinal ends on the frame.

During a surgical procedure, the tray is covered in a sterile material, and instruments to be used during surgery are placed on the tray. Then, as the instruments are required for the procedure, each is picked up from the tray by the surgeon, or an assistant hands the requested instrument to the surgeon.

SUMMARY OF THE INVENTION

The present invention provides a neutral field tray (NFT) attachable to a mayo stand for supporting a surgical instrument during a variety of surgical procedures, and a method of using the NFT. The surgical instruments used in such procedures include a proximal end defining a handle portion, and a distal end for acting on a patient. Such distal end may include a blade, needle or other sharp.

The NFT includes an attachment portion for removably attaching the NFT to the frame of a mayo stand, a base coupled to the attachment portion, sidewalls extending upward from opposite sides of the base along the length of the base between proximal and distal ends, a distal endwall extending upward from the distal end of the base between the sidewalls, a cover extending between the sidewalls above the base adjacent the distal endwall, and support for positioning the surgical instrument such that handle of the instrument is oriented toward the hand of the medical professional, and the medical professional's hand is protected from the sharp at the distal end of the instrument.

In one embodiment, the attachment portion of the NFT defines a hook or other structure which extends over a portion of the frame of a standard mayo stand such that a mayo tray can be seated on the frame over the attachment portion of the NFT. The attachment portion of the NFT may resiliently clip onto the frame of the mayo stand and/or be sandwiched between the frame and the mayo tray. In addition, the attachment portion of the NFT may define at least one hook which couples the NFT to a portion of the frame.

When mounted to the mayo stand, the NFT allows a doctor or assistant to place the surgical instrument in the NFT with a distal end of the instrument disposed under the cover, and a proximal end of the instrument openly accessible. In addition, the NFT orients the proximal end of the surgical instrument such that the distal end is oriented sloped downward relative to the proximal end. In one embodiment, the base of the NFT is preferably sloped downward at an angle relative to the horizontal frame of the mayo stand when the NFT is attached to the mayo stand. The downward sloping of the base of the NFT ergonomically orients the instrument for insertion and retrieval. In one embodiment, the instrument is preferably elevated relative to the base to facilitate retrieval from the NFT by providing a plurality of longitudinally spaced supports along the length of the base. In another embodiment, the base includes tapered side portions which direct the sharp of the instrument into a protective trough that extends below the floor of the tray.

The mounted NFT allows a surgical assistant to move a surgical instrument from the mayo tray (or other source) to the NFT and position the instrument in the NFT in the orientation described above. A doctor may then remove the instrument from the NFT, perform a surgical procedure, and return it to the NFT in the same manner for either removal and disposal or return to the mayo tray (or other location) by an assistant.

As further discussed below, the structure of the NFT, the positioning of the NFT on the mayo stand relative to a doctor and assistant, and the method employed by the doctor and assistant in using the NFT all reduce the risk of injury to the doctor, assistant, patient, and any others present in the operating room.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
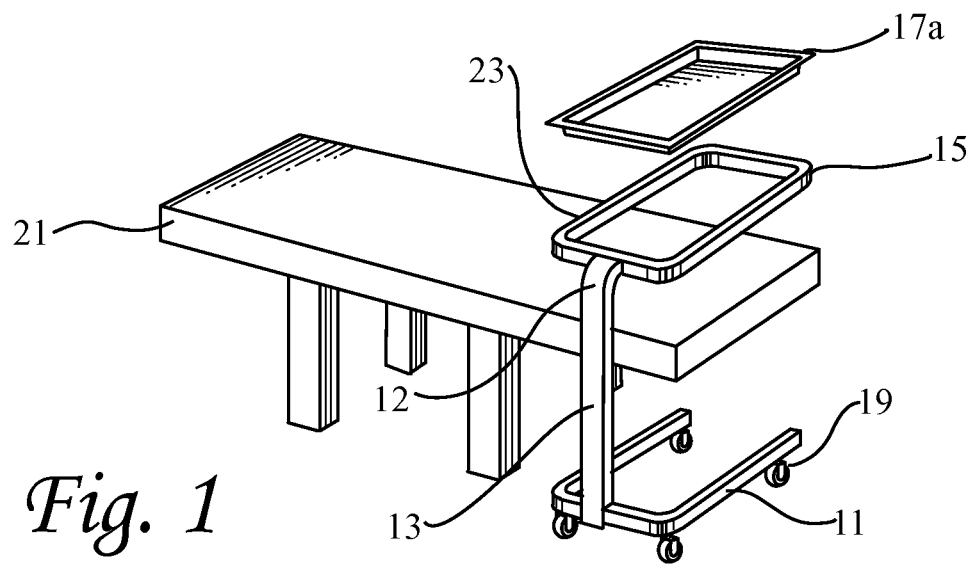
FIG. 1 is an operating table and partially exploded mayo stand and tray positioned about the operating table.

Turning now to FIGS. 1-4, a first embodiment of a neutral field tray (NFT) 10 is shown attached to a mayo stand 12 for supporting a surgical instrument 14 during a variety of surgical procedures.

The mayo stand 12 (FIG. 1) to which the NFT 10 attaches has a base 11 with wheels 19, a vertical leg 13 extending upward from the base 11, and a generally horizontal rectangular frame 15 attached to the vertical leg 13. The frame 15 has an upper surface 15a and a lower surface 15b. The frame 15 horizontally supports a mayo tray 17a (FIGS. 1, 5-6) or table 17b (FIG. 4), which rests on the upper surface 15a of the frame 15, and is used by scrub nurses or other assistants to hold/support instruments and supplies during surgery. The mayo stand 12 and horizontal tray 17a or table 17b thus provide a stable horizontal surface that is movable relative to an operating table 21 while remaining at a uniform height above the operating table 21.

Figure 2:
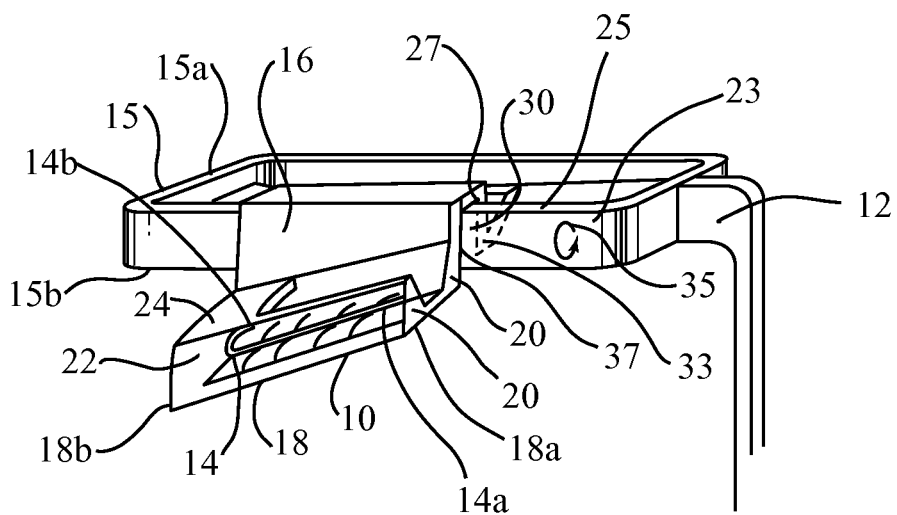
FIG. 2 is a mayo stand with a neutral field tray attached thereto according to the invention.

Referring primarily to FIG. 2, the NFT 10 includes an attachment portion 16 for removably attaching the NFT 10 to the mayo stand 12, a base 18 coupled to the attachment portion 16, sidewalls 20 extending upward from opposite sides of the base 18 along the length of the base between proximal and distal ends (18a, 18b), a distal endwall 22 extending upward from the distal end 18b of the base 18 between the sidewalls 20, a cover 24 extending between the sidewalls 20 above the base 18 adjacent the distal endwall 22, and support 26 (FIGS. 3A-3D) for positioning the surgical instrument 14 above the base 18.

Figure 3A:
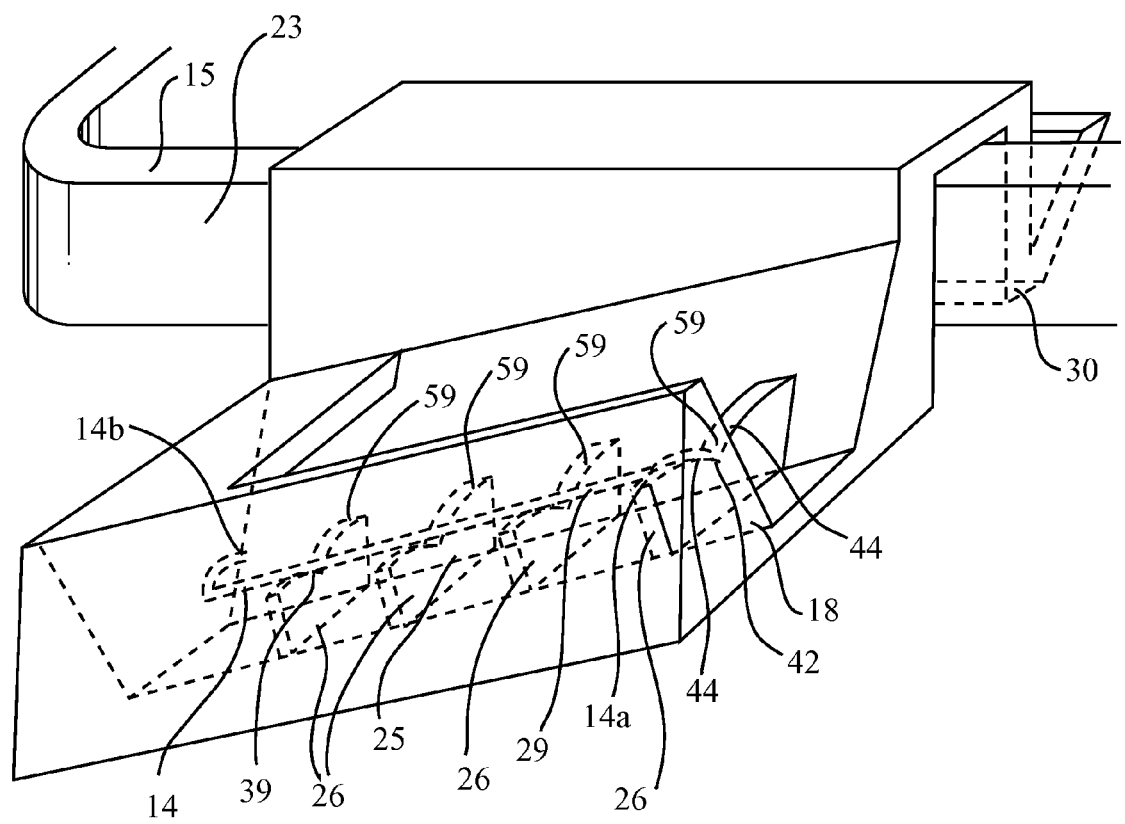
FIG. 3A is an enlarged view of the neutral field tray of FIG. 2 attached to a sidewall of the mayo stand and showing longitudinally displaced ridges supporting a surgical instrument.

The NFT 10 is either a single molded unit or multi-component unit made from a preferably firm plastic, paper, cardboard or other cellulose-based materials, or other inexpensive but sufficiently stiff material (i.e., to be shape retaining) which is safe for use during operating procedures and preferably sufficiently inexpensive to be disposable on a single-use basis. The NFT 10 is sized to accommodate typical sharp instruments used in the operating room which are potentially dangerous for hand-to-hand transfer, such as scalpels, needles, and other instruments typically used during surgical procedures. The base 18 of the NFT 10 is preferably approximately ten inches long and four inches wide, as such will accommodate a single instrument as well as access to such instrument by a doctor, though other suitable dimensions may be used. The sidewalls 20 of the NFT 10 are preferably 2 inches high relative to the base 18 and may be angled inward toward the center of the base 18. As shown in FIGS. 2 and 3A, the top of the NFT 10 is preferably open except for the cover 24 adjacent the distal endwall 24. The base 18, sidewalls 20, distal endwall 22, and cover 24 together define a box portion which protects the hand of a doctor or assistant from accidental contact with the sharp distal end 14b of the surgical instrument 14, and a proximal opening allows the instrument 14 to be removed from the NFT 10. To this end, the cover 24 is preferably situated close enough to the base 18 to limit entry of an adult human hand into the box portion defined by the base 18, sidewalls 20, distal endwall 22, and cover 24; i.e., to prevent human hand contact with the sharp at the distal end of the instrument.

The attachment portion 16 of the NFT 10 extends from one of the sidewalls 20 and defines a channel 30 which clips onto a sidewall 23 of the frame 15 of the mayo stand 12. The channel 30 is preferably defined small enough to prevent the NFT 10 from rotating off of the sidewall 23 (e.g., the narrow channel 30 and fairly rigid inner side 33 of the attachment portion 16 maintain the NFT 10 attached to the sidewall 23 under the force of gravity). For example, when the attachment portion 16 of the NFT 10 is clipped onto the sidewall 23 of the mayo stand 12, gravity will pull the NFT 10 downward. The top edge 25 of the sidewall 23 will catch in the corner 27 and the NFT 10 will rotate about the top edge 25 in the direction of the arrow 35 until the outer side 37 of the attachment portion 16 contacts the sidewall 23, at which point the NFT 10 will be anchored to the sidewall 23. If the channel 30 is very narrow (roughly equal to the width of the top edge 25) then the NFT 10 will not rotate at all about the sidewall 23. Further, the channel 30 can be sized slightly narrower than the width of the sidewall 23, and the inner side 33 and adjacent sidewall 20 can be flexed relative to each other to seat over the sidewall 23 and then be resiliently retained on the sidewall 23 in an interference fit.

Figure 4:
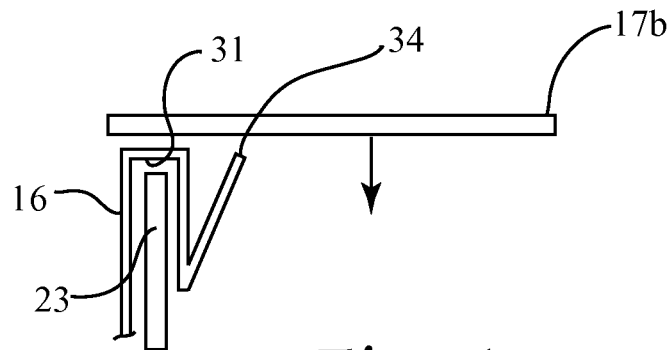
FIG. 4 is a side view of the attachment portion of the neutral field tray of FIG. 2 sandwiched between the mayo tray and the sidewall of the mayo stand.
Figure 5:
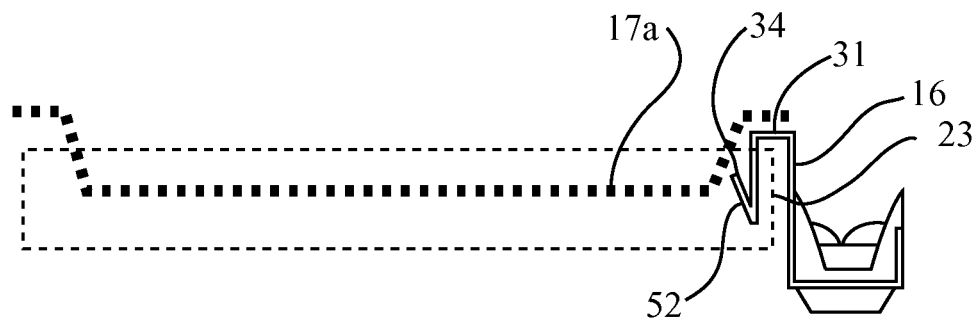
FIG. 5 is a side view of the neutral field tray of FIG. 2 assembled with the mayo stand and a mayo tray.

As most clearly shown in FIGS. 4-5, the NFT 10 may also be supported by the horizontal table 17b (or tray 17a), the weight of which sandwiches the top portion 31 of the attachment portion 16 of the NFT 10 between the table 17b and the sidewall 23 of the frame 15. As shown, the attachment portion 16 also preferably defines an inner flange 34 disposed underneath and in close proximity to or touching the mayo tray 17a or table 17b. When assembled to the frame, the table 17b preferably maintains the top portion 31 generally parallel with the table 17b and also optionally contacts the top of the inner flange 34 of the attachment portion 16. It will be appreciated that such a configuration prevents significant rotation of the NFT 10 about the sidewall 23. Additionally, it will be appreciated that sterile material which is typically placed over the mayo table 17b and tucked under the table 17b will help to hold the NFT 10 in place.

Figure 6:
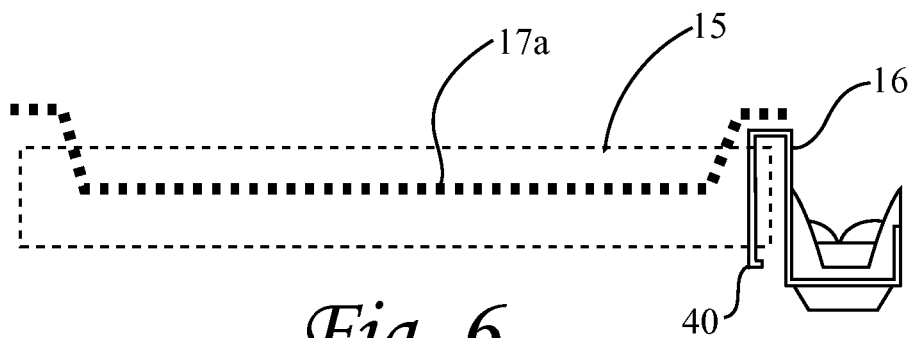
FIG. 6 is a side view of another embodiment of the neutral field tray of the invention in which the attachment portion defines hooks which hook onto a mayo stand.

Turning to FIG. 6, in one embodiment, the attachment portion 16 of the NFT 10 may define at least one hook 40 which catches on or extends slightly below the bottom of the frame 15 of the mayo stand 12 when the NFT 10 is attached to the frame 15.

Turning back to FIGS. 2 and 3A, once mounted to the mayo stand 12, the NFT 10 allows a doctor or assistant to place the surgical instrument 14 in the NFT 10 with a distal end 14b of the instrument disposed under the cover 24, and a proximal end 14a of the instrument elevated relative thereto. The base 18 of the NFT 10 is preferably sloped downward at an oblique angle of 10-40 degrees relative to the horizontal frame 15 of the mayo stand 12 when the NFT 10 is attached to the mayo stand 12. The downward sloping of the base 18 of the NFT 10, which preferably orients the distal end of the base 18 and support 25 below the lower surface 15b of the frame, ergonomically orients the instrument 14 for insertion and retrieval.

The base also includes a support 25 (FIG. 3A) to elevate the instrument 14 relative to the base to facilitate manipulating instrument in the NFT. The support 25 preferably comprises longitudinally displaced ridges 26 which define grooves 42 shaped to receive the handle 29 and/or body 39 of the surgical instrument 14, as well as curved top surfaces 44 on opposite sides of the respective grooves 42 which slope downward toward the respective grooves 42. The ridges 26 support the surgical instrument 14 above the base 18 so that a person retrieving the instrument 14 from the NFT 10 can more easily secure the instrument 14 with his or her fingers. At least two to four ridges 26 approximately ⅛" high relative to the base 18 are preferably provided, though other numbers and heights may be used. The grooves 42 and curved top surfaces 44 limit lateral movement of the surgical instrument 14 once it is positioned in the NFT 10 within the grooves 42. In addition, the supports may be of different sizes to supplement (or be used instead of) the angle of the base relative to the frame. For example, if larger supports are used at the proximal end and smaller supports are used at the distal end, such will have the effect of positioning the instrument in a distal end sloped down orientation. The slope of the base 18 and/or the configuration of the support 25 provides that the distal end of the instrument 14 is gravity fed toward the end wall 22 of the tray.

Figure 3B:
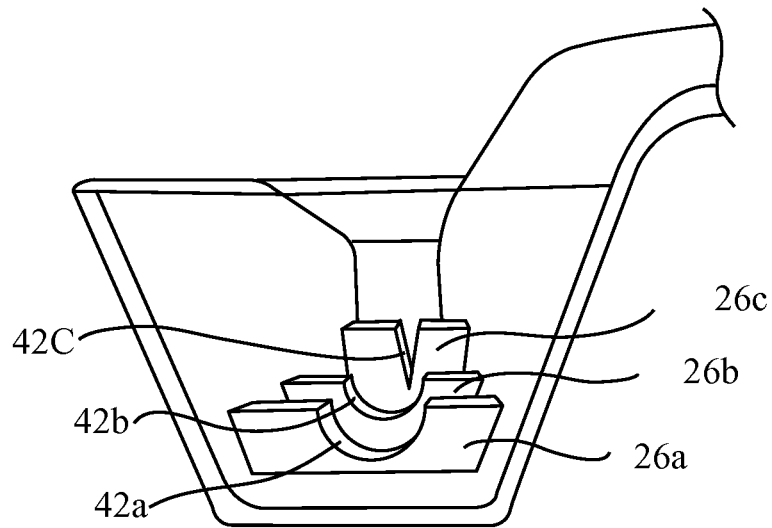
FIG. 3B is an end view of the neutral field tray with proximal ridges defining curved grooves and a distal ridge defining a straight groove.

While general use grooves 42 are shown in FIG. 3A, the grooves 42 of a particular ridge 26 may vary in size and shape according to the location of the particular ridge 26 along the base 18 of the NFT so as to accommodate the instrument(s) 14 which will be used by the doctor for a given surgical procedure. For example, as shown in FIG. 3B, the proximal-most and central-most ridges 26a, 26b each define a curved groove 42a, 42b and the distal-most ridge 26c defines a straight groove 42c. The grooves may extend partially through the supports (e.g., FIGS. 3B-3D) or extend all the way through to the base of the tray (142c in FIG. 8).

Figure 3C:
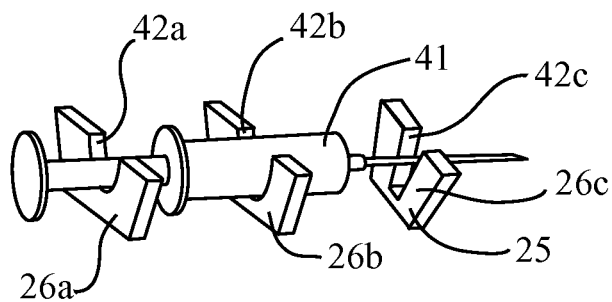
FIG. 3C illustrates the ridges of FIG. 3B with a syringe placed therein.

As shown in FIG. 3C, when a syringe 41 is placed within the ridges 26a, 26b, 26c, the wider piston pump of the syringe rests on and is supported within the proximal curved grooves 42a, 42b, and the needle of the syringe extends through the distal groove 42c, which is preferably a vertical slot. The curved proximal grooves 42a, 42b prevent lateral movement of the syringe within the NFT 10.

Figure 3D:
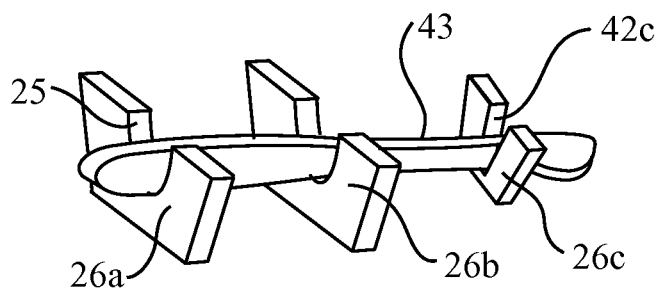
FIG. 3D illustrates the ridges of FIG. 3B with a scalpel placed therein.

As shown in FIG. 3D, when a thin scalpel 43 is placed within the ridges 26a, 26b, 26c, the distal slot 42c at the distal end of the NFT 10 orients the blade and handle portion of the scalpel 43 longitudinally along the NFT 10 with its thickest dimension transverse relative to the base 18 of the NFT 10 (e.g., the distal slot 42c preferably defines a channel smaller than the thickest dimension of the scalpel 43, and thus does not allow the scalpel 43 to be rotated ninety degrees or to be moved laterally).

Figure 7:
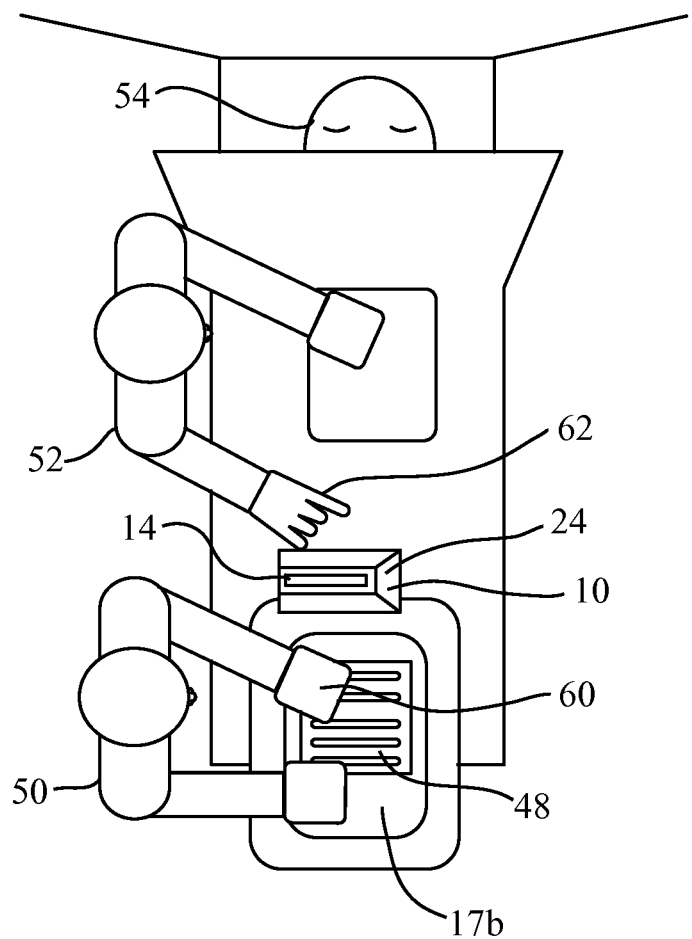
FIG. 7 is an illustration of an embodiment of the neutral field tray as part of an operating room setup.

Turning to FIG. 7, the mounted NFT 10 allows an assistant 50 to move a surgical instrument from a store 48 of instruments on the mayo tray 17b to the NFT 10 and position the instrument in the NFT 10 in the orientation described above. A doctor 52 may then remove the instrument 14 from the NFT 10, perform a surgical procedure, and return it to the NFT 10 in the same manner for removal and disposal or return to the mayo tray 17b by the assistant 50. At no time is the instrument passed directly from hand-to-hand between doctor and assistant. The NFT 10 thus creates a "neutral field" between the doctor 52 and assistant 50 as further discussed below.

Figure 8:
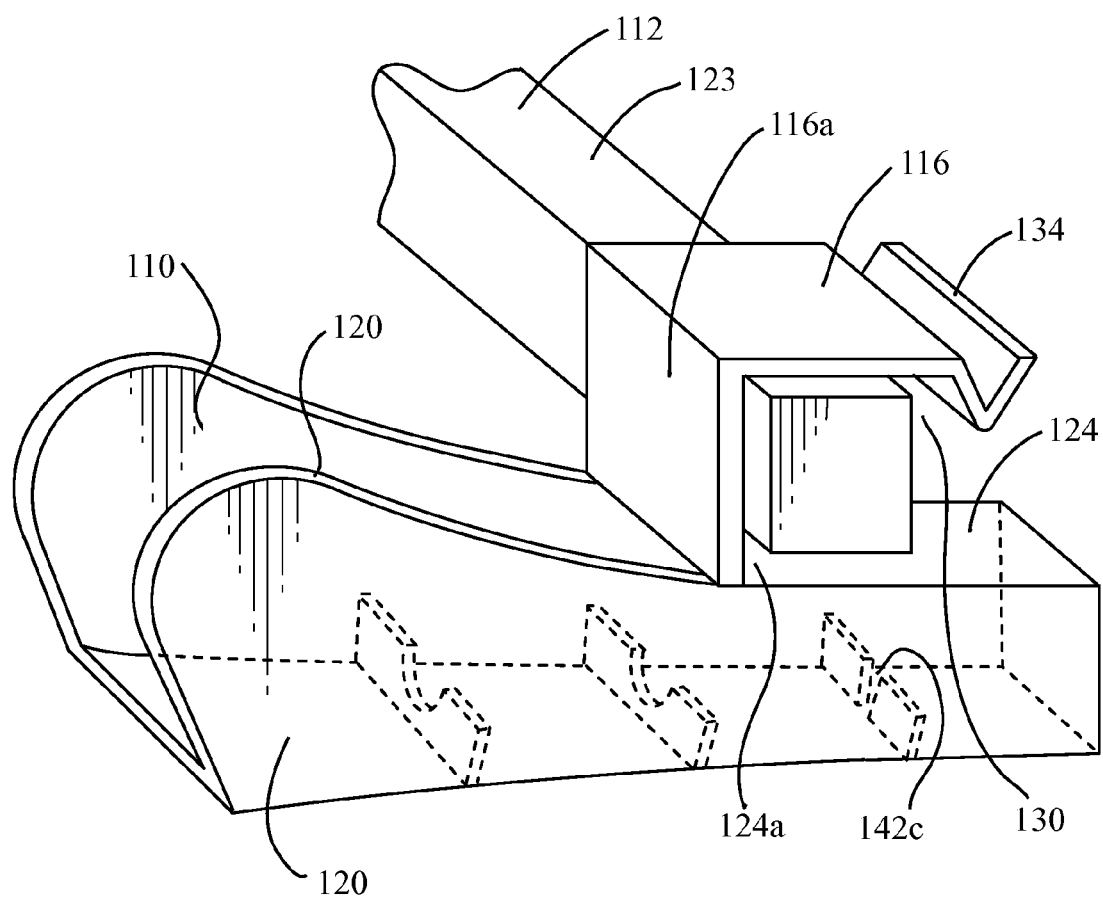
FIG. 8 is a view of yet another embodiment of the neutral field tray in which the attachment portion extends from the cover of the tray.

Turning to FIG. 8, in another embodiment, a neutral field tray (NFT) 110 has an attachment portion 116 which extends from a proximal end 124a of the cover 124 to a distal flange 134. In this embodiment, the NFT 110 is still preferably formed as a single piece of material with the attachment portion 116 defining a channel 130 extending in a direction transverse to the longitudinal direction of the NFT 110 and bounded at the bottom by the top of the cover 124. The NFT 110 has a flared proximal opening with sidewalls 120 which curve at the top to create rounded edges. The NFT 110 clips to a sidewall 123 of the mayo stand 112. The channel 130 is preferably defined small enough to prevent the NFT 110 from rotating off of the sidewall 123. In this embodiment, the channel 130 is preferably sized smaller than the height of the sidewall 123, and the attachment portion 116 can be flexed relative to the cover 124 to clip the NFT 110 to the sidewall 123 with sufficient force to hold the NFT 110 in place. As discussed above with respect to FIGS. 4 and 5, the NFT 110 may be held by a horizontal table or tray, the weight of which sandwiches the attachment portion 116 between the table and the sidewall of the frame. Additionally, sterile material placed over the table may grip a proximal wall 116a of the attachment portion 116.

Figure 9:
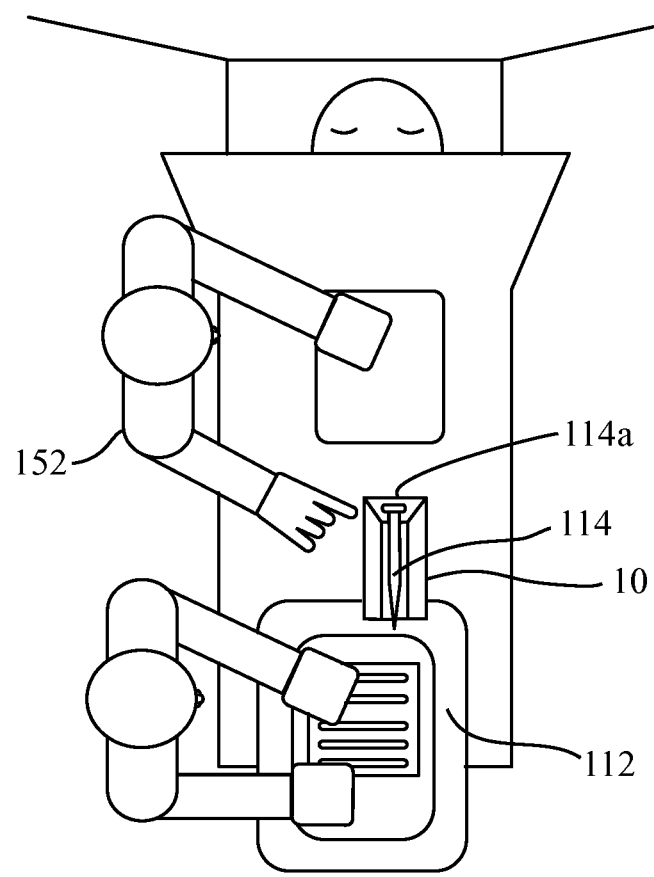
FIG. 9 is an illustration of an embodiment of the neutral field tray of FIG. 8 as part of an operating room setup.
Figure 10A:
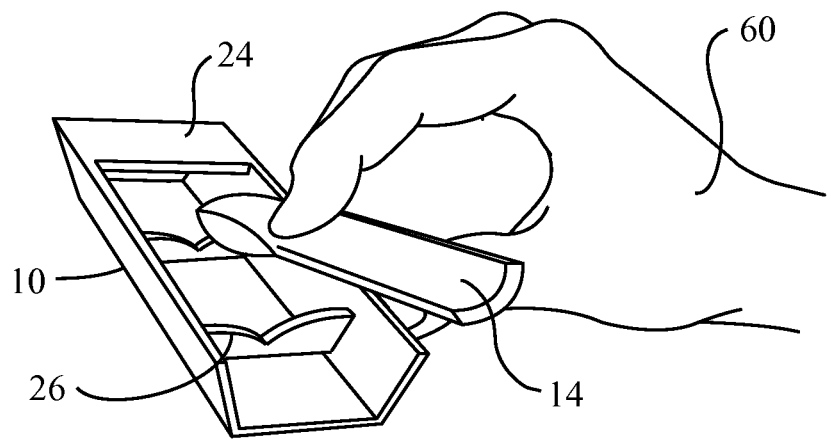
FIG. 10A is an illustration of an assistant's hand placing a surgical instrument into the neutral field tray.
Figure 10B:
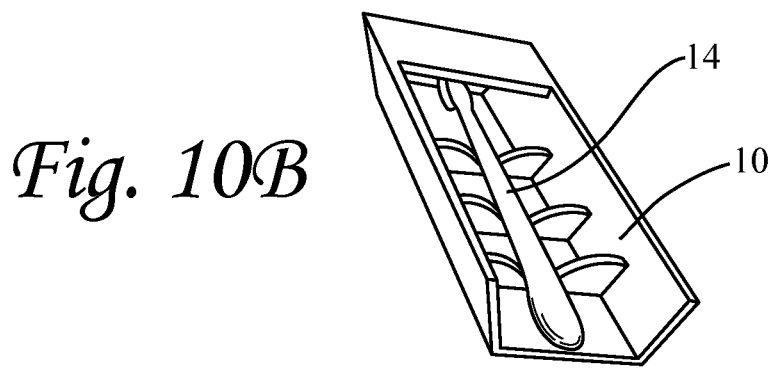
FIG. 10B is an illustration of the surgical instrument supported inside the neutral field tray.
Figure 10C:
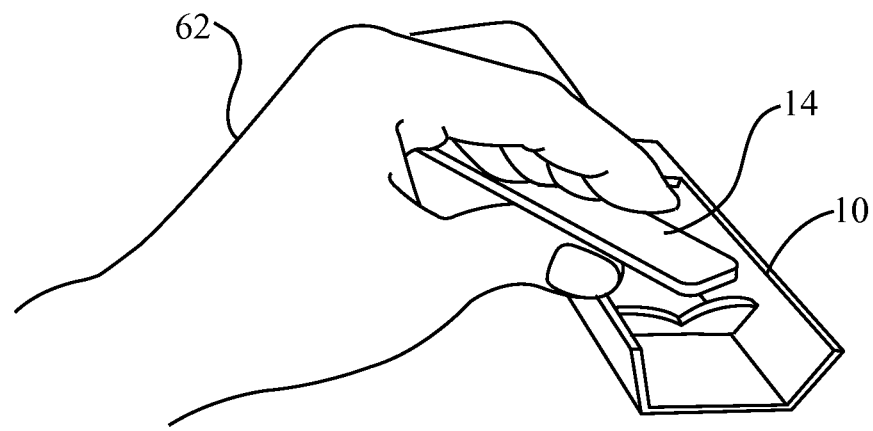
FIG. 10C is an illustration of a doctor's hand removing the surgical instrument from the neutral field tray.
Figure 11:
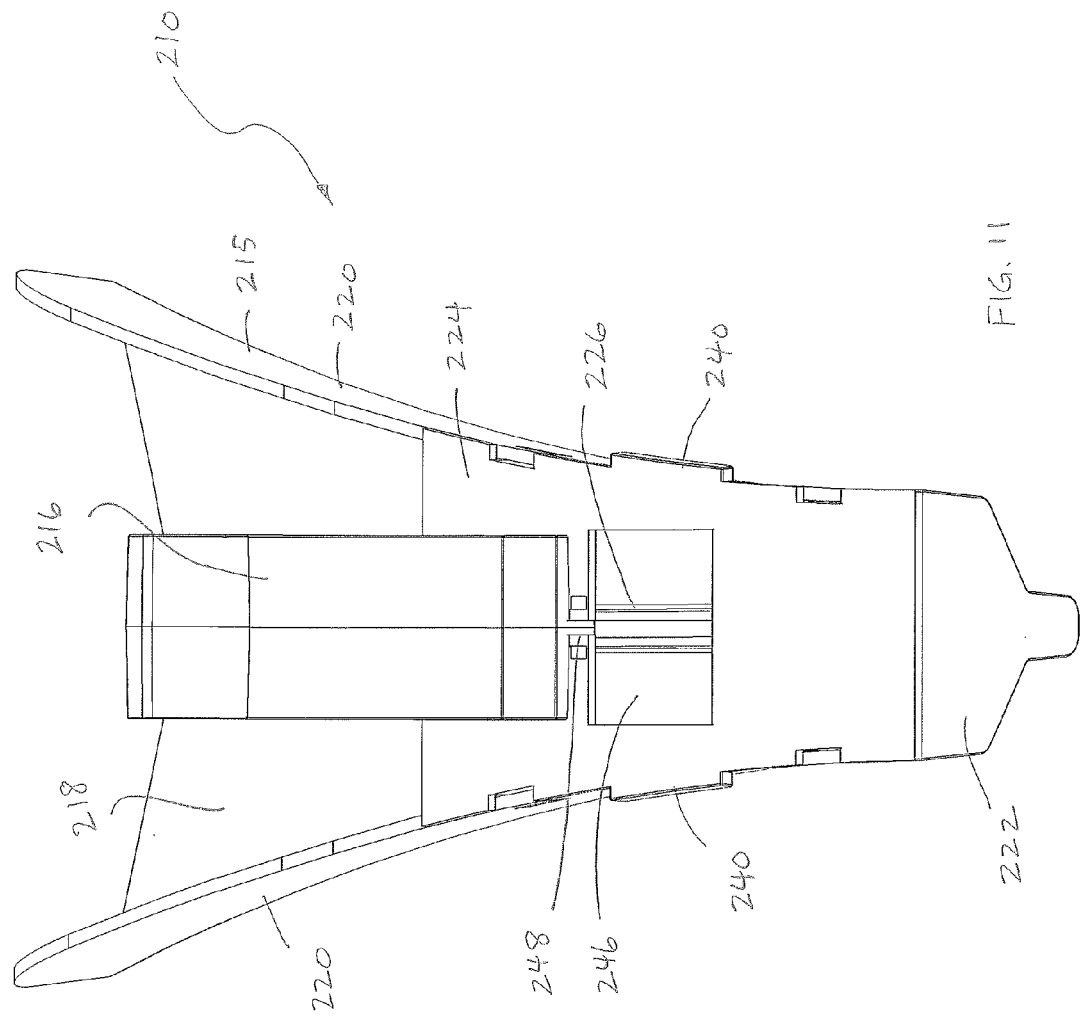
FIG. 11 is a distal end view of another embodiment of a neutral field tray, wherein the tray is shown oriented at an orientation when mounted to the mayo stand; i.e., in use.
Figure 12:
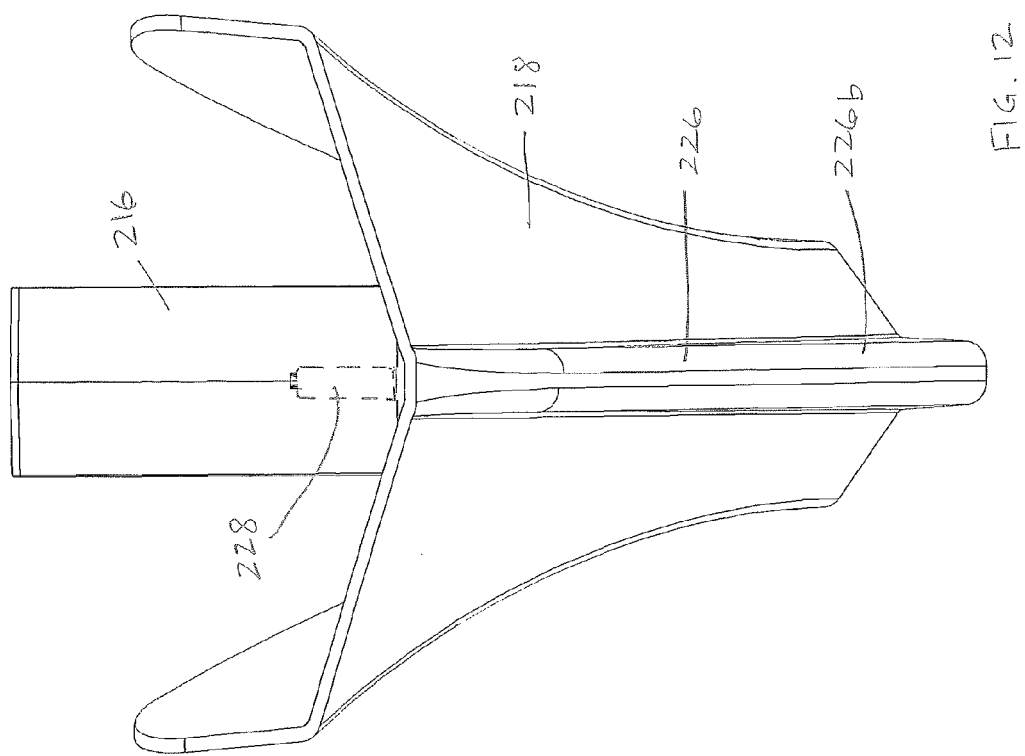
FIG. 12 is a proximal end view of the neutral field tray of FIG. 11, wherein the tray is shown at the same orientation as FIG. 12.
Figure 13:
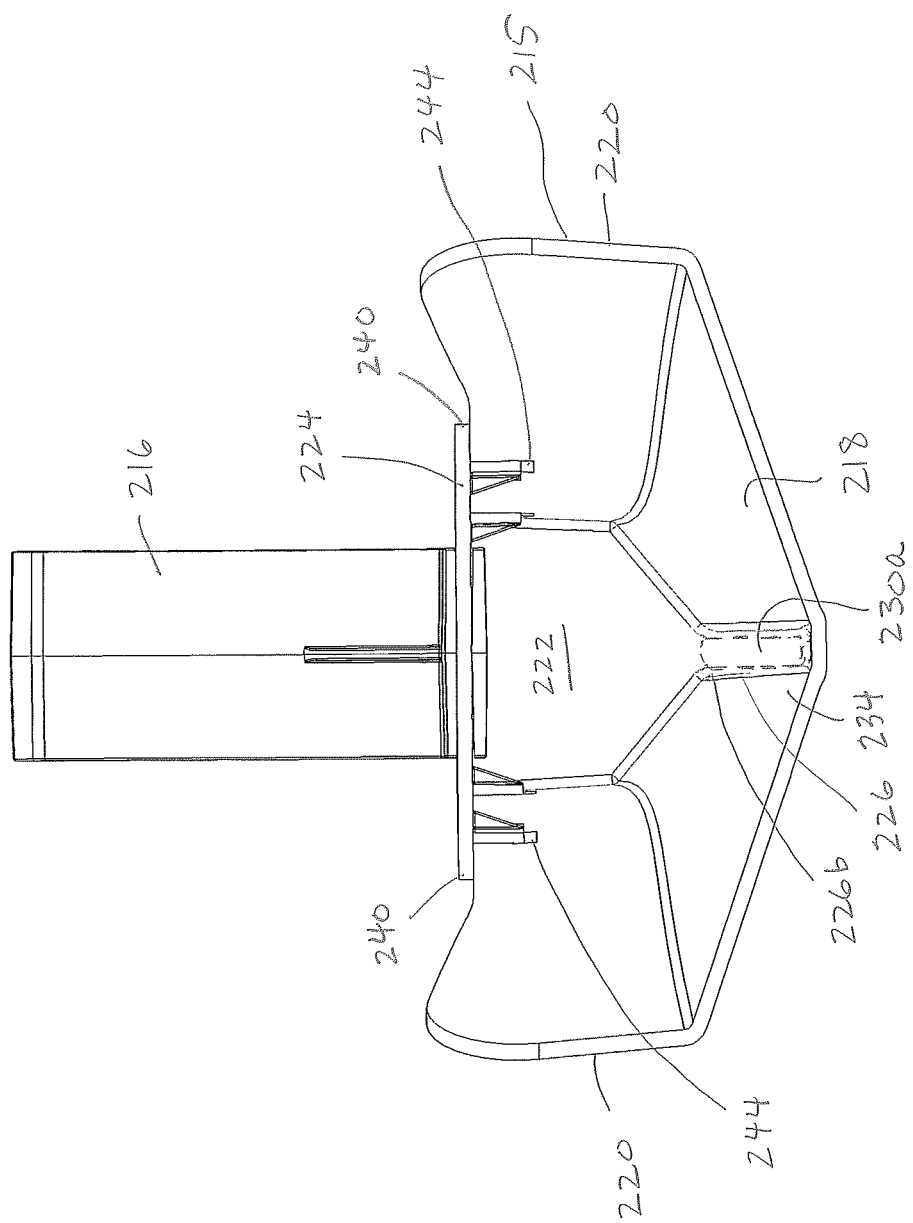
FIG. 13 is a proximal end view of the neutral field tray of FIG. 11, wherein the tray is shown rotated downwards out of its mayo stand mounted orientation.
Figure 14:
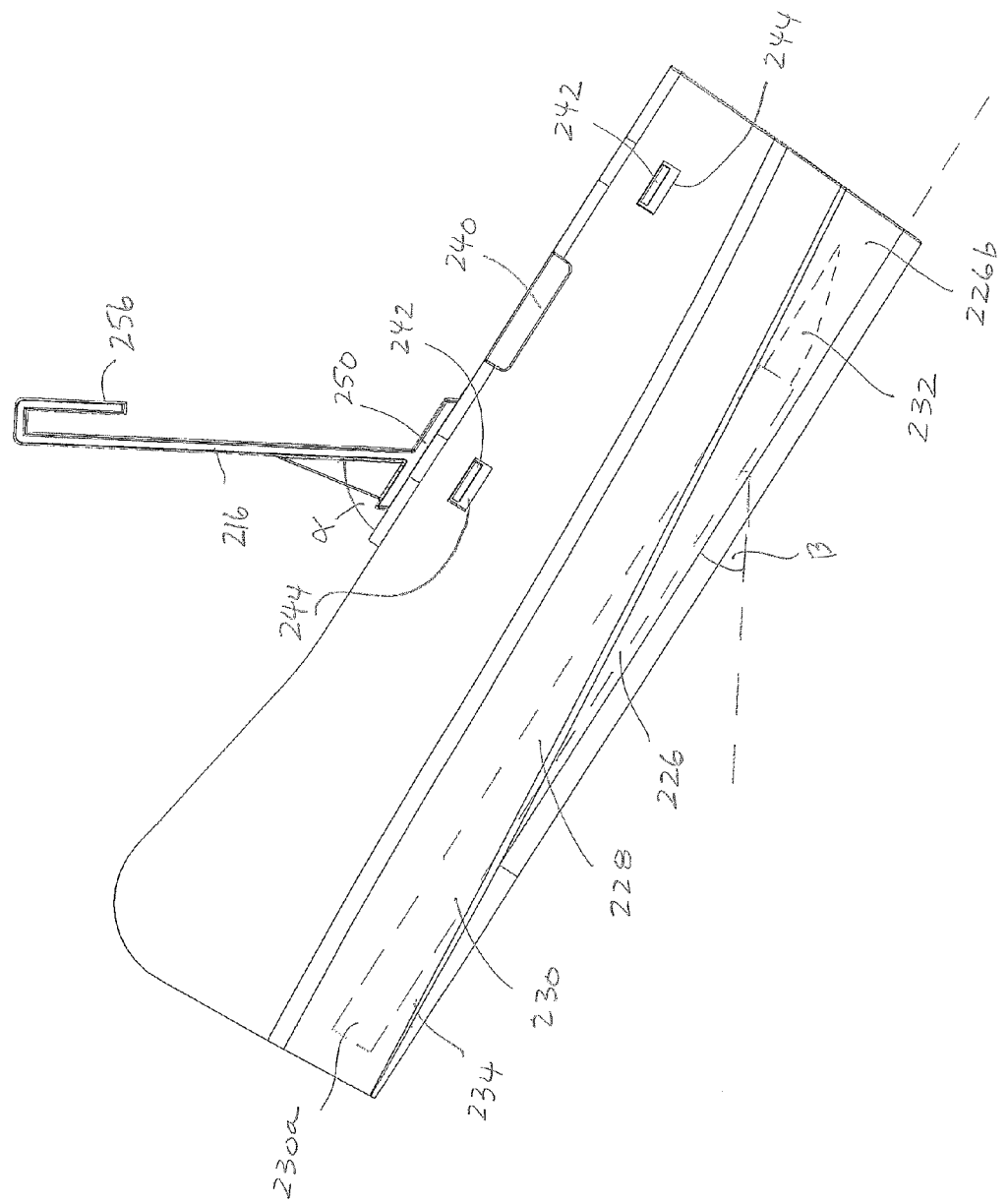
FIG. 14 is a side elevation view of the neutral field tray of FIG. 11, wherein the tray is shown oriented at the same orientation as FIG. 12.
Figure 15:
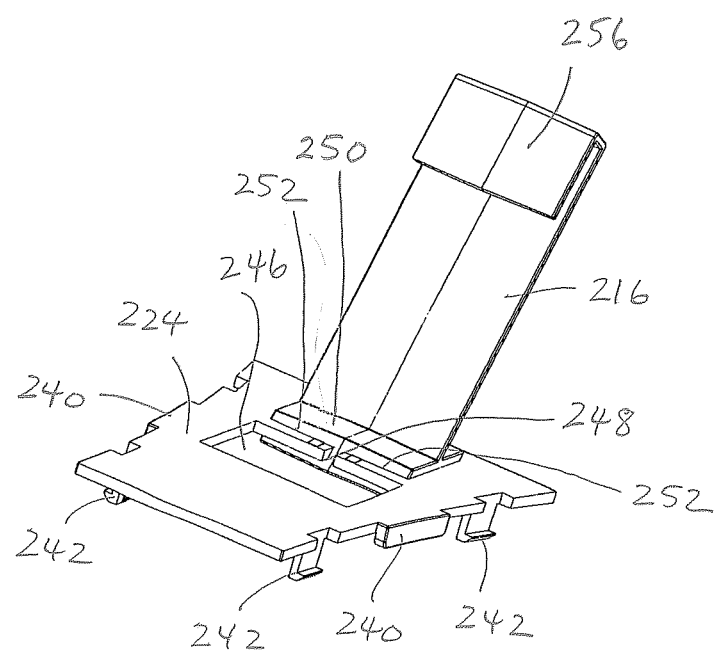
FIG. 15 is a rear perspective view of the cover and attachment portion of the neutral field tray of FIG. 11.

Turning to FIG. 9, the NFT 110 of FIG. 8, when mounted to the mayo stand 112 in an operating room layout, orients the medical instrument 114 with a proximal end 114a in very close proximity to the doctor 152 for easy access.

Referring now to FIGS. 11 through 15, yet another embodiment of a neutral field tray (NFT) 210 is shown. NFT 210 shown includes three discrete elements: a tray 215, a tray cover 224 extending over a portion of the tray 215, and an attachment portion 216 which is connected to the cover 224 for coupling the NFT 210 to a mayo stand. Alternatively, the NFT 210 may be constructed as a unitary structure from a single piece of material, from two elements or from more than three elements.

The tray 215 includes a base or floor 218, side walls 220, and a distal end wall 222. The floor 218 slopes down from the side walls 220 toward a medial portion of the tray, and also tapers in width toward the distal end wall 222. The floor 218 also defines a central trough 226 of preferably uniform width and which gradually deepens toward the distal end wall 222. The trough 226 is sized to accommodate a single surgical instrument at a time, such as a scalpel 228, in a stable and readily accessible orientation. For example, scalpel 228 has a handle 230 with a generally rectangular cross-section, i.e., with a height that is substantially greater than its width. The trough 226 is sized to receive the scalpel handle 230 such that the blade 232 at the distal end of the scalpel 228 is retained in an upright orientation. The depth of the trough at the proximal end 234 of the tray is shallow (or the trough may terminate prior to the proximal end) such that the proximal handle 230a is exposed and properly oriented for easy grasp by the surgeon. Meanwhile, the distal trough 226b is preferably sufficiently deep to recess the entirety of the blade 232 below the floor 218. Due to the slope of the floor 218 downward from the sidewalls 220 and obliquely angled downward relative to the horizontal frame, the instrument 230 is gravity fed from the floor into the trough 226 (with the handle 230a oriented upright and the blade 230b always situated within the recess of the trough) and with the distal blade end 230b of the instrument moving to the distal end of the trough. Other instruments are similarly accommodated. For example, when a syringe is located into the NFT 210, the trough is sized to stably support the barrel of the syringe, while the sharp is recessed within the trough in a safe manner below the remainder of the floor.

The cover 224 extends between the side walls 220 above the floor 218 adjacent from approximately midway along the proximal-distal dimension of the side walls 220 to the end wall 222. The cover 224 includes shoulders 240 situated to seat about an upper portion of the side walls 220, as well as tabs 242 that engage holes 244 in side walls 220 of the tray to stably lock the cover to the tray 215. The cover 224 includes a central opening 246 leading into a slot 248.

The attachment portion 216 is attached to the cover 224 via the opening 246 and slot 248. The attachment portion 216 includes a lower end 250 defining deep recesses 252 extending into laterally extending sides 254 of the lower end 250 so that the lower end assumes a squat I-beam shape. The lower end 250 is received through the opening 246 in the cover 224 and portions of the cover on each lateral side of the slot 248 engage within the recesses 252 to form an interference fit that secures the attachment portion 216 to the cover 224. The attachment portion includes a J-hook 256 extending upward from the lower end 250. The J-hook 256 is adapted in size and shape to seat over the horizontal frame 15 of a mayo stand (FIG. 1). Alternatively, different structure, such as a clip, can be provided to the attachment portion to otherwise engage the frame 15 of the mayo stand. Moreover, the attachment portion may connect to the side walls, rather than the cover (as described above), with the J-hook or other structure appropriately oriented to couple the tray to the frame of the mayo stand. The J-hook 256 extends at an oblique angle α relative to the cover 224 (e.g., 40° to 75°, and more preferably 60°) so that bottom of the trough 226 in the floor 218 of the tray is oriented at an oblique angle β relative to a horizontal plane (e.g., 20° to 45°, and more preferably 30). In this manner the handle 230 of the surgical instrument (e.g., scalpel 228) is oriented upwards at a corresponding ergonomically advantageous angle, while the sharp 232 of the instrument is oriented downward.

Figure 16:
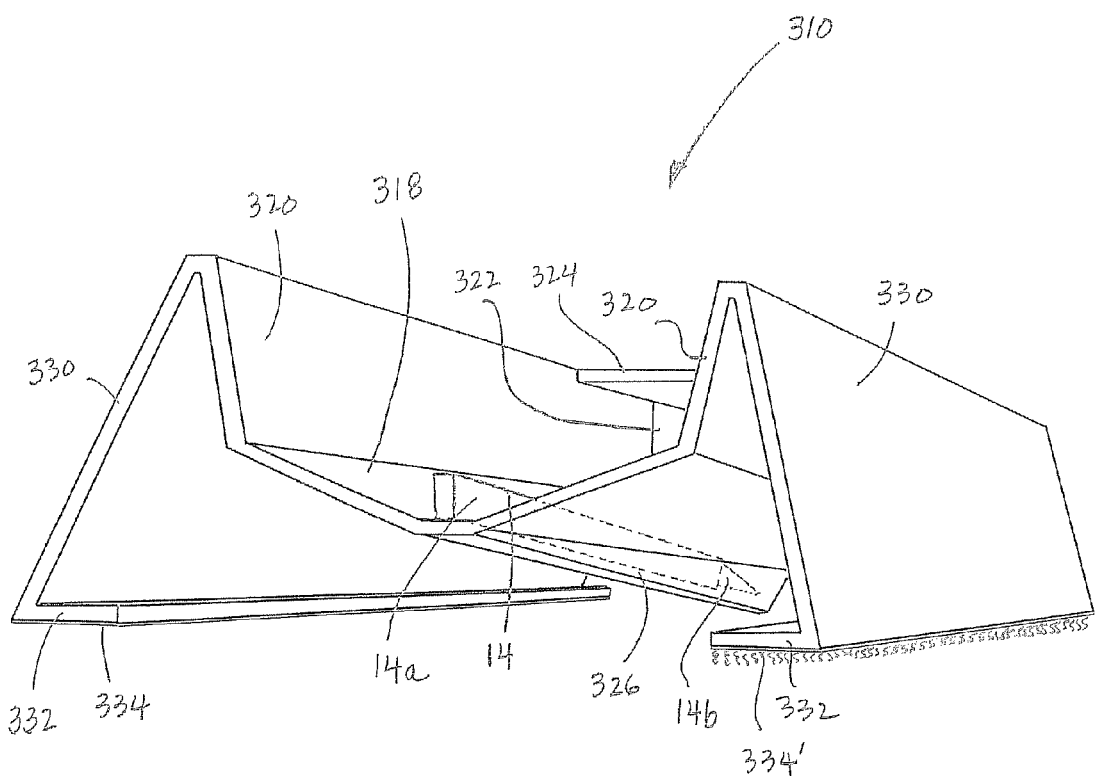
FIG. 16 is proximal end perspective view of yet another embodiment of a neutral field tray according to the invention.

Turning now to FIG. 16, another embodiment of a neutral field tray 310 is shown. The NFT 310 has a base 318, trough 326, side walls 320, end wall 322, and cover 324 in substantially a same tray structure configuration as the NFT 210. That is, the base 318 has a proximal end and a distal end and defines a length between its proximal and distal ends. The trough 326 extends longitudinally in a proximal-distal direction (preferably along the longitudinal axis of the base) and is at least partially recessed relative to the base 318. The base 318 has a downward slope transverse to the length of the base and toward the trough. The trough 326 is sized to receive at most a single instrument 14, and is angled relative to the base 318 so as to orient such instrument in the proximal-distal direction with its proximal handle end 14a elevated relative the distal sharp end 14b. The sidewalls 320 extend upward from opposite sides of the base 318 between the proximal and distal ends of the base 318. The distal endwall 322 extends upward from the distal end of the base between the two sidewalls 320. The cover 324 extends over the base 318 between at least a distal portion of the sidewalls 320 and adjacent the distal endwall 322 so as to cover the distal sharp end of the instrument 14b.

However, in distinction from the NFT 210, NFT 310 does not include an attachment portion for coupling to a frame of a mayo stand. Rather, NFT 310 includes a support structure for seating the above-defined tray structure on a surface, including a table or tray. The support may include outer walls 330 that descend downward from the sidewalls 320 (such that in the shown embodiment the NFT has a M-shaped cross-section transverse to its proximal-distal axis). Such support may further include a lower flange 332 provided to the bottom of the outer walls 330 to increase stability when seated on a surface. Moreover, such support may also include an adhesive 334, hook and loop fastener, 334' (shown on the same figure for the convience but more practically provided as an alternate embodiment), or other securing means to couple the NFT 310 to the surface during a surgical procedure. The securing means may be temporary or even permanent, as the tray may be used over a drape that will be disposed of together with the tray after the surgical procedure. Alternatively other supporting structure can be provided. By way of one example, the supporting structure may include a structure that extends down from one side wall 320 and then under the base 318 like a large supporting flange. By way of another example, the supporting structure may include a structure that extends down from the endwall 322 and then angles back under the base 318. By way of yet another example, the supporting structure may be in the form of a tripod. Further, the distal lower end of the trough 326 may define one of the three supports of the tripod. Other supporting structure(s) can likewise be provided to support the tray on a suitably stable surface.

Referring now to FIGS. 7, 9, and 10A-10C, one preferred protocol for using the NFT 10 (or 110 or 210 or 310) is as follows. The assistant 50 uses his hand 60 to move a surgical instrument 14 from the mayo tray 17b (or other source) to the NFT 10 and position the instrument 14 in the NFT 10 with the distal end 14b of the instrument disposed under the cover 24. As described above, the instrument 14 is then gravity fed to be situated upright with the sharp 14b located under the cover 24 of the NFT. The doctor 52 then uses his hand 62 to remove the instrument 14 from the NFT 10 and perform a surgical procedure with the instrument 14 on a patient 54. The doctor 52 then returns the instrument 14 to the NFT 10 and the instrument 14 is positioned within the NFT 10 with the distal end 14b of the instrument disposed under the cover 24. The assistant then removes the instrument 14 from the NFT 10, ready to present the next instrument into the NFT 10 upon request by the doctor 52. The method is repeated until the surgical procedure on the patient 54 is completed.

As shown in FIGS. 10A-10C and 3A-3D, the size of the NFT 10 and the support 25, as shown by the ridges 26a-26c and grooves 42a-42c (or via trough 226 in FIGS. 12-14 or trough 326 in FIG. 16), are preferably configured to receive at most one surgical instrument 14 at a time. This eliminates any possible confusion or injury to the doctor 52, assistant 50, or patient 54 which might otherwise occur if multiple instruments were left in the NFT 10.

The fixed location of the NFT 10 relative to the doctor 52 and assistant 50 facilitates the surgical procedure and reduces the risk of injury. The location of the NFT 10 remains unchanged throughout the procedure.

The protection of the sharp distal end 14b of the surgical instrument 14 by the cover 24, the positioning of the NFT 10 on the mayo stand 17b between the doctor 52 and assistant 50, and the employment of the method discussed above for using the NFT 10 facilitates transfer of instruments by at least reducing the risks of instruments being dropped during transfer and increases safety in the operating room by reducing the risk of doctors and their assistants from being punctured by the sharps of instruments during instrument transfer.

There have been described and illustrated herein several embodiments of a NFT and methods of using the same. While particular embodiments of the invention have been described, it is not intended that the invention be limited thereto, as it is intended that the invention be as broad in scope as the art will allow and that the specification be read likewise. Thus, while particular shapes and dimensions of a neutral field tray have been disclosed, it will be appreciated that other shapes and dimensions may be used as well. In addition, while longitudinally displaced ridges have been disclosed for supporting a surgical instrument, it will be appreciated that other types of support may be used. Also, while particular angles have been disclosed for orienting the base of the field tray relative to the mayo stand, and for orienting a surgical instrument, it will be recognized that other angles may be used as well. Furthermore, while specific positioning of a neutral field tray in an operating room relative to a doctor and an assistant has been disclosed, it will be understood that other layouts in an operating room can be similarly used. Also features shown with respect to one NFT can be used in combination with the other. It will therefore be appreciated by those skilled in the art that yet other modifications could be made to the provided invention without deviating from its spirit and scope as claimed.

What is claimed is:

1. A neutral field tray for use in association with a surgical instrument having a proximal end and a distal end provided with a sharp, the neutral field tray comprising:
    a base having a proximal end and a distal end and defining a length between said proximal and distal ends;
    an instrument trough longitudinally extending in the proximal-distal direction and at least partially recessed relative to said base, said base having a downward slope transverse to the length of said base toward said trough, wherein said trough is sized to receive at most a single surgical instrument, said trough angled in the proximal-distal direction relative to said base such that when the surgical instrument supported in said trough has its distal end oriented toward said distal end of said base, the proximal end of the surgical instrument is elevated relative to the distal end of the surgical instrument,
    two sidewalls extending upward from opposite sides of said base between said proximal and distal ends;
    a distal endwall extending upward from said distal end of said base between said two sidewalls; and
    a cover extending between a portion of said sidewalls above said base and adjacent said distal endwall, said cover configured to cover the sharp at the distal end of the instrument when the instrument is positioned in said trough.

2. A neutral field tray according to claim 1, wherein:
said trough exposes the proximal handle and shields the sharp at the distal end of the instrument.

3. A neutral field tray according to claim 2, wherein:
said trough has an open proximal end.

4. A neutral field tray according to claim 2, wherein:
said trough extends along a longitudinal axis of said base.

5. A neutral field tray according to claim 1, wherein:
a width is defined between said two sidewalls, and said width between said sidewalls tapers from said proximal end to said distal end.

6. A neutral field tray according to claim 1, wherein:
said base, said two sidewalls, said distal endwall, and said cover together define a box portion and a proximal opening to said box portion.

7. A neutral field tray according to claim 6, wherein:
said proximal opening of said box portion is sized to prevent entry of a human hand into said box portion to a location at which the distal end of the instrument is situated.

8. A neutral field tray according to claim 1, further comprising:
the surgical instrument.

9. A neutral field tray for use in association with a surgical instrument having a proximal end and a distal end provided with a sharp, the neutral field tray comprising:
    a base having a proximal end and a distal end and defining a length between said proximal and distal ends;
    two sidewalls extending upward from opposite sides of said base between said proximal and distal ends, said base having a downward slope away from at least one of said sidewalls, said slope oriented transverse to said length of the base;
    one and only one instrument trough provided at least partially recessed relative to the base and sized and configured to support at most a single surgical instrument with the distal end of the instrument at a distal end of said trough and a proximal end of the instrument at a proximal end of said trough, said proximal end of said trough being open;
    a distal endwall extending upward from said distal end of said base between said two sidewalls;
    a cover extending between said sidewalls above said base and adjacent said distal endwall; and
    supporting structure for supporting said neutral field tray relative to a supporting surface.

10. A neutral field tray according to claim 9, wherein:
said supporting structure includes a hook for attaching said tray to a frame of a mayo stand.

11. A neutral field tray according to claim 10, wherein:
when said supporting structure is coupled to the frame of the mayo stand, said trough is located below the frame of the mayo stand.

12. A neutral field tray according to claim 10, wherein:
when said supporting structure is coupled to the frame of the mayo stand, said trough is located within the footprint of the frame of the mayo stand.

13. A neutral field tray according to claim 9, wherein:
said supporting structure includes at least one outer wall extending downward from said sidewalls.

14. A neutral field tray according to claim 13, wherein:
said at least one outer wall includes a lower supporting flange angled relative to said at least one outer wall.

15. A neutral field tray according to claim 14, further comprising:
said flange is provided with a hook and loop fastener.

16. A neutral field tray according to claim 14, wherein:
said flange is provided with an adhesive.

17. A neutral field tray for use in association with a surgical instrument having a proximal end and a distal end provided with a sharp, the neutral field tray comprising:
    a non-flat base having a proximal end and a distal end and defining a length between said proximal and distal ends, said base defining a width that tapers from said proximal end to said distal end;
    one and only one instrument trough provided at least partially recessed relative to the base and sized and configured to support at most a single surgical instrument with the distal end of the instrument at a distal end of said trough and a proximal end of the instrument at a proximal end of said trough, said proximal end of said trough being open, said trough obliquely oriented relative to said base so as to present the proximal end of the instrument substantially above said base and to shield the sharp of the instrument within the trough; and
    supporting structure for supporting said neutral field tray relative to a supporting surface.

18. A neutral field tray according to claim 17, wherein:
when the instrument is positioned on said base, said non-flat surface of said base operates to gravity feed the instrument into said trough.

19. A neutral field tray according to claim 17, further comprising:

a distal endwall at said distal end of said trough.

20. A neutral field tray according to claim 19, further comprising:

a cover extending over a distal end of said base, such that when the instrument is positioned in said trough, said trough further shields the sharp of the instrument.

\* \* \* \* \*